(12) United States Patent
Marino

(10) Patent No.: US 6,540,747 B1
(45) Date of Patent: Apr. 1, 2003

(54) SYSTEM FOR SECURING JOINTS TOGETHER

(75) Inventor: James F. Marino, La Jolla, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/549,807

(22) Filed: Apr. 14, 2000

Related U.S. Application Data

(60) Provisional application No. 60/167,189, filed on Nov. 23, 1999, and provisional application No. 60/129,703, filed on Apr. 16, 1999.

(51) Int. Cl.[7] ............................................. A61B 17/70
(52) U.S. Cl. .............................. 606/61; 606/73; 606/80
(58) Field of Search .............................. 606/61, 72, 73, 606/79, 80

(56) References Cited

U.S. PATENT DOCUMENTS

| | | | |
|---|---|---|---|
| 4,541,423 A | | 9/1985 | Barber |
| 4,781,181 A | | 11/1988 | Tanguy |
| 4,878,915 A | * | 11/1989 | Brantigan ..................... 606/53 |
| 4,907,577 A | | 3/1990 | Wu |
| 5,470,333 A | | 11/1995 | Ray |
| 5,476,463 A | | 12/1995 | Boachie-Adjei et al. |
| 5,527,312 A | * | 6/1996 | Charles ......................... 606/61 |
| 5,562,735 A | | 10/1996 | Margulies |
| 5,571,189 A | * | 11/1996 | Kuslich .................... 623/17.12 |
| 5,591,170 A | | 1/1997 | Spievack et al. |
| 5,643,320 A | * | 7/1997 | Lower et al. ................ 606/104 |
| 5,702,452 A | | 12/1997 | Argenson et al. |
| 5,713,900 A | | 2/1998 | Benzel et al. |
| 5,728,097 A | | 3/1998 | Mathews |
| 6,099,529 A | * | 8/2000 | Gertzman et al. ............ 606/72 |

OTHER PUBLICATIONS

Chiu et al., Feb. 1999, www.spinecenter.com/abstracts.htm, www.spinecenter.com/papers/facet/facet.htm.*
http://ortharth.toronto.on.ca/oai/care3a_gx.htm.*

* cited by examiner

Primary Examiner—David O. Reip
Assistant Examiner—D Jacob Davis
(74) Attorney, Agent, or Firm—Jonathan Spangler

(57) ABSTRACT

A system for securing first and second opposing facet joints together, comprising: a cannulated drill having a side opening; and an extendible member received within the cannula of the cannulated drill, the extendible member having a distal end which passes out of the side opening in a direction radially outwards from the axis of the cannulated drill as the extendible member is advanced distally through the cannula of the drill. The drill can be rotated such that the extendible member ablates opposite contacting surfaces of first and second facet joints, promoting fusion between the first and second facet joints. A facet screw passing through a hole drilled by the cannulated drill through the first facet joint and into the second facet joint is tightened into position to immobilize the first and second facet joints together.

11 Claims, 9 Drawing Sheets

SYSTEM FOR SECURING JOINTS TOGETHER

CROSS-REFERENCES TO RELATED APPLICATIONS

The present application is a regular patent application of and claims the benefit of priority from U.S. patent application Ser. Nos. 60/167,189 filed Nov. 23, 1999 and U.S. Ser. No. 60/129,703 filed Apr. 16, 1999, the full disclosures of which are incorporated herein by reference.

TECHNICAL FIELD

The present invention relates in general to spinal fixation systems and in particular to facet screw systems for securing adjacent facet joints together.

BACKGROUND OF THE INVENTION

Facet screws are used to secure a patient's facet joints together, thus preventing relative movement between adjacent facet joints. Such facet screws are typically used during various spinal surgery procedures such as discectomy with posterior instability; degenerative disc disease; degenerative joint disease in the facet joint; and general instability, both to prevent relative movement of the facet joints (thus promoting arthrodesis) and to provide support and stability to the vertebral level (thus promoting arthrodesis).

Other benefits of facet joint screws are that they can be used to stabilize the spine in lieu of more expensive and surgically time consuming instrumentation, for example, pedicle screw systems.

A common disadvantage with existing facet screw systems are that they must be used in conjunction with other stabilization systems, for example, anterior strut grafts or other inorganic implants, to provide sufficient stability to the patient's vertebrae after surgery and also that they require a difficult surgical procedure to safely place them.

SUMMARY OF THE INVENTION

The present invention provides systems for securing a pair of facet joints together. An advantage of the present invention is that by immobilizing opposing adjacent facet joints with respect to one another it provides stability for vertebral arthrodesis, as is desired, for example, after a medical procedure such as a discectomy with fusion.

In accordance with the present invention, a system is provided to position a facet screw to secure a patient's opposite adjacent first and second facet joints together, and to promote fusion therebetween.

In a preferred aspect, the facet screw is positioned to secure together the inferior articular process of the first facet joint and the superior articular process of the second facet joint, with the facet screw positioned to pass from a posterior approach through the first facet joint toward the pedicle of the second facet joint. This embodiment is called the transfacet approach. Other approaches for facet screw placement are also contemplated (i.e. the translaminar approach).

In a preferred aspect of the present invention, the contacting surfaces of the adjacent facet joints are ablated (to promote fusion) prior to the facet screw being inserted (to securely hold the facet joints together). An advantage of the present system of ablation is that it utilizes the natural healing response of the facet bones, where the ablated contacting surfaces of the facet joints will tend to fuse together after such ablation.

In a preferred aspect of the present invention, the opposite contacting surfaces of the facet joints are ablated by an extending member which protrudes radially outwardly from a drill (at a location between the opposite contacting surfaces). Preferably, the drill from which the extending member protrudes is the same drill which is used to drill a hole for the facet screw placement.

Most preferably, the extending member comprises a flexible wire which is received in a cannulated passageway in the drill. In this preferred aspect of the invention, the drill preferably has a side hole and the extending member (i.e.: the flexible wire) is advanced distally through a cannulated passage in the drill such that the wire's distal end protrudes radially outwardly through the side hole in the drill.

In this aspect of the invention, the drill is advanced through the first facet joint and into the second facet joint to a depth such that it's side hole is positioned between the opposite contacting surfaces of the first and second facet joints.

Thereafter, the extending member is advanced to protrude outwardly to a desired radial distance from the drill, such that further rotation of the drill will cause the extending member to rotate in a circular path around the drill, thereby ablating a rather large surface area of the opposite contacting surfaces of the first and second facet joints. The specific size of the ablated region on each of the opposite contacting surfaces on the first and second facet joints will depend upon the length to which the distal end of the extending member is advanced to protrude outwardly from the drill.

Accordingly, an advantage of the present drill being adapted such that an extending member can be deployed therefrom (e.g.: through a side hole therein) is that a rather large area of the facet joint surfaces can be accessed and thereby ablated, yet requiring only a standard sized drill hole as would typically be used to insert a standard facet screw.

In optional aspects of the present invention, the facet screw is introduced into the patient in a cannulated posterior approach. In such aspects of the invention, the drill may be advanced through an operating cannula such that a distal end of the drill commences drilling at a posterior point on the inferior articular process of the first facet joint.

In yet another optional aspect of the present invention, the drill itself is dimensioned (i.e.: tapered) to drill a countersink into the first facet joint, such that the head of the facet screw can be received substantially flush against the first facet joint. Consequently, the head of the facet screw can be positioned out of the way of surrounding tissues.

In yet another optional aspect of the present invention, the drill (and the facet screw) are positioned in a preferred posterior approach into the patient by way of a surgical guidance platform, with the drill and the facet screw being sequentially advanced through an operating cannula which is supported by the surgical guidance platform.

In yet another optional aspect of the present invention, the extending member is advanced into the facet joint between the opposing contact surfaces of the first and second facet joints by means of a cannulated delivery device (rather than a drill).

In an optional preferred aspect of the present invention, the extendible member may comprise a wire made of a shape memory metal, such as Nitinol, but is not so limited as other suitable materials may instead be used.

DESCRIPTION OF THE SPECIFIC EMBODIMENTS

Figure 1:
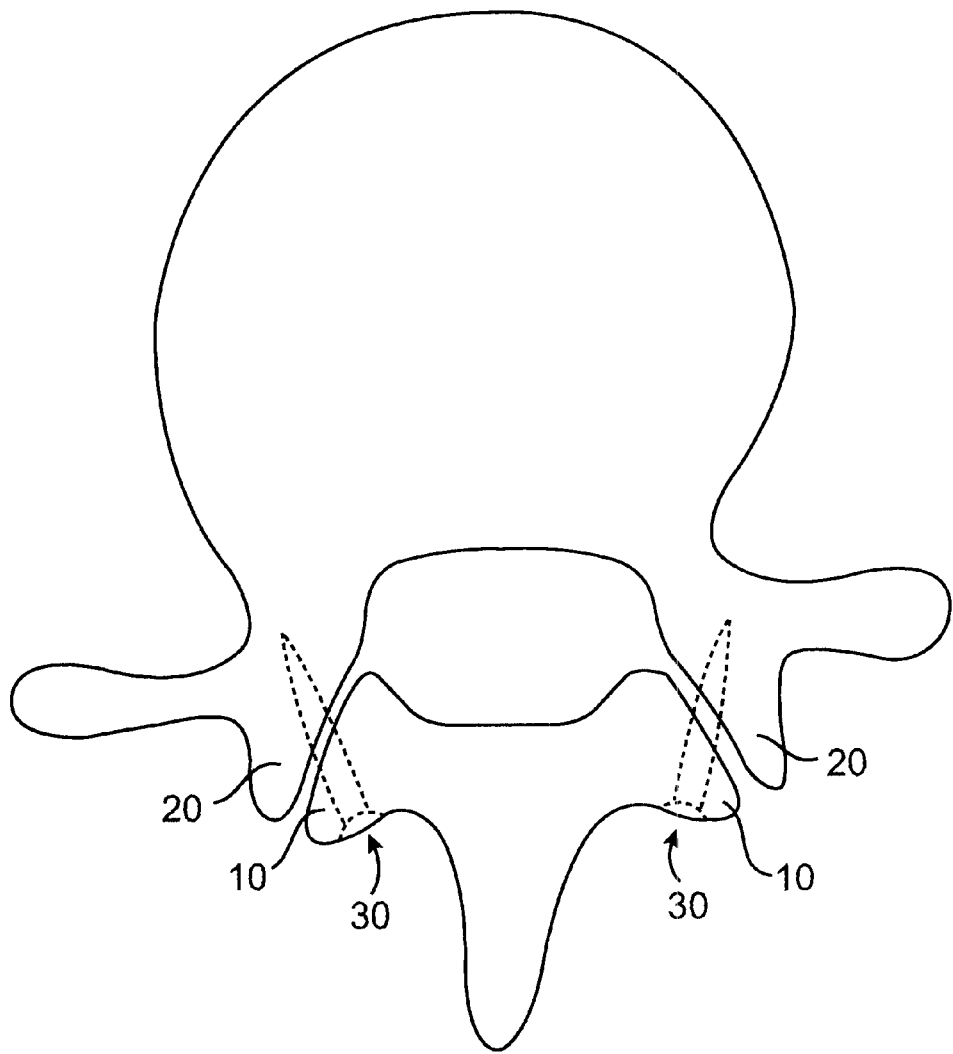
FIG. 1 is a top view of first and second facet joints being held together by a facet screw, showing a preferred angle of placement of the facet screw.
Figure 2A:
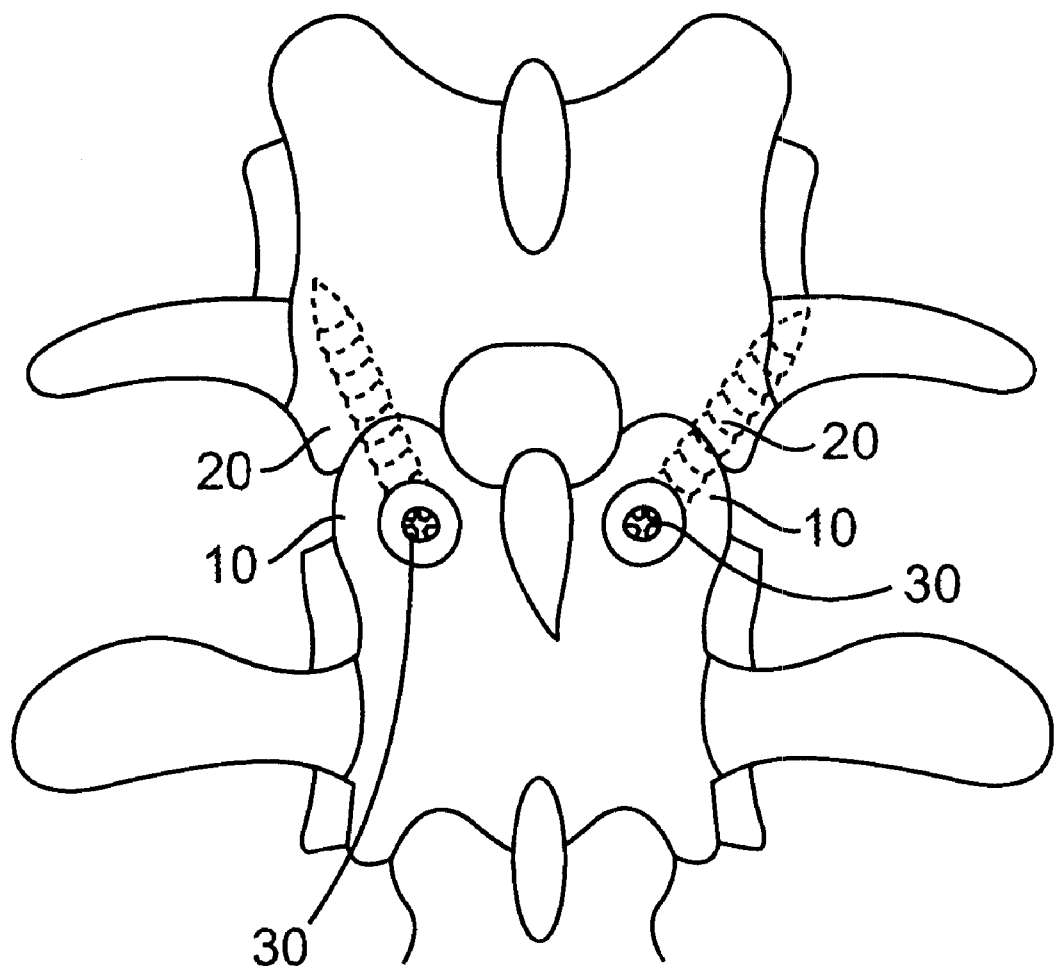
FIG. 2A is a side (anterior-posterior) view of first and second facet joints being held together by a facet screw, showing a preferred angle of placement of the facet screw.
Figure 2B:
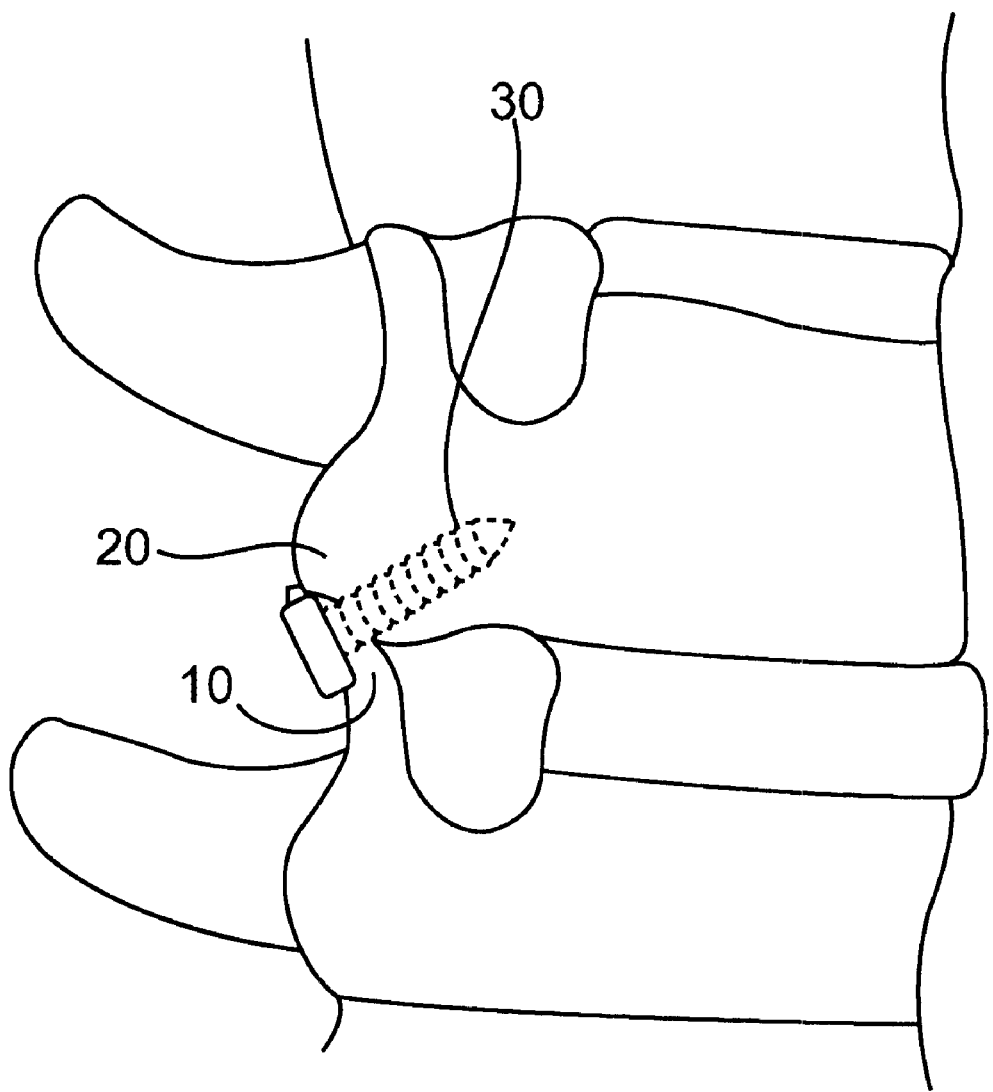
FIG. 2B is a side (lateral) view of first and second facet joints being held together by a facet screw, showing a preferred angle of placement of the facet screw.

In accordance with the present invention, a pair of opposing facet joints may be secured together by a system comprising a facet screw. Referring to FIGS. 1, 2A and 2B, first facet joints 10 and second facet joints 20 are secured together by a pair of facet screws 30. As illustrated, facet screws 30 are positioned in a posterior approach with respect to the patient, however, other approaches into the patient are also contemplated. As illustrated, first facet joint 10 preferably comprises a patient's inferior articular process and second facet joint 20 comprises a patient's superior articular process.

FIGS. 3 to 7 show sequential steps in placing facet screw 30 such that it passes through first facet joint 10 and into second facet joint 20 (as was shown in FIGS. 1, 2A and 2B). When tightened into position, facet screw 30 will immobilize first facet joint 10 and second facet joint 20 together.

Figure 3:
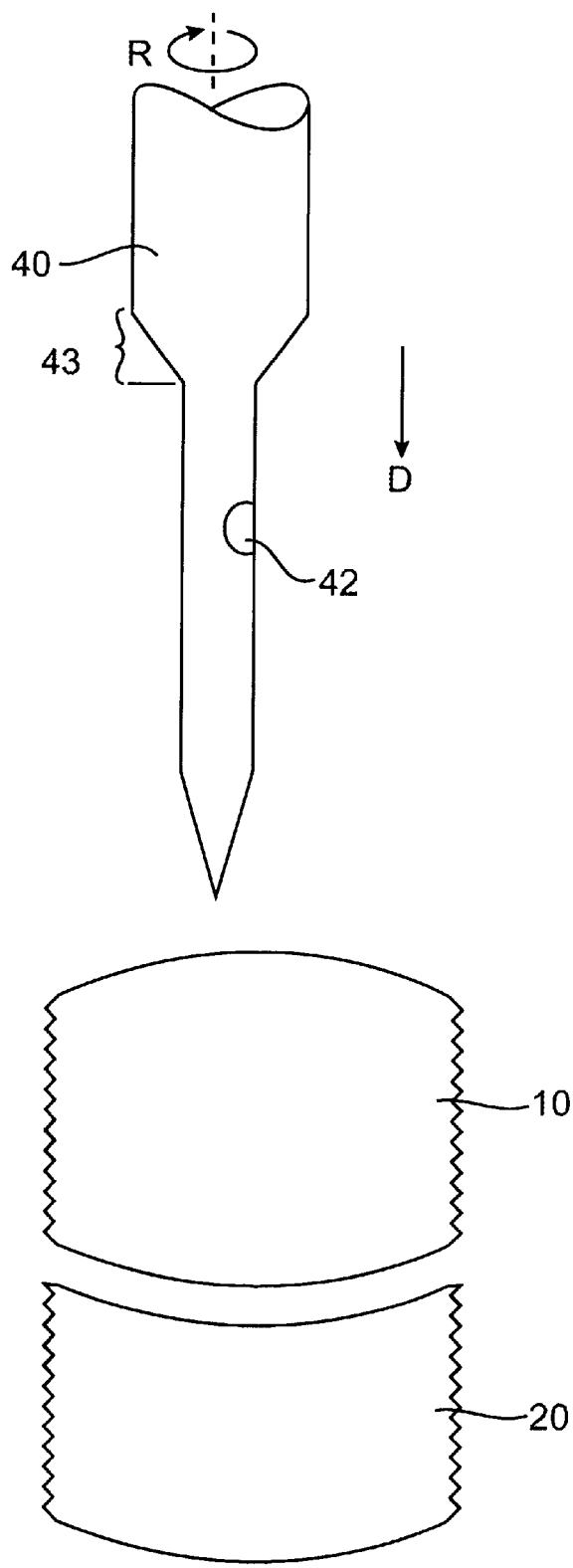
FIG. 3 is an illustration of a drill being advanced towards a first facet joint.

Referring to FIG. 3, a cannulated drill 40 is first positioned to drill a hole for the facet screw. Placement of cannulated drill 40 in a preferred orientation (for example, in a preferred posterior approach) with respect to the patent can be achieved by using a surgical guidance platform such as the platform set forth in co-pending U.S. patent application Ser. No. 09/326,739 filed Jun. 4, 1999, incorporated herein by reference in its entirety.

Figure 4:
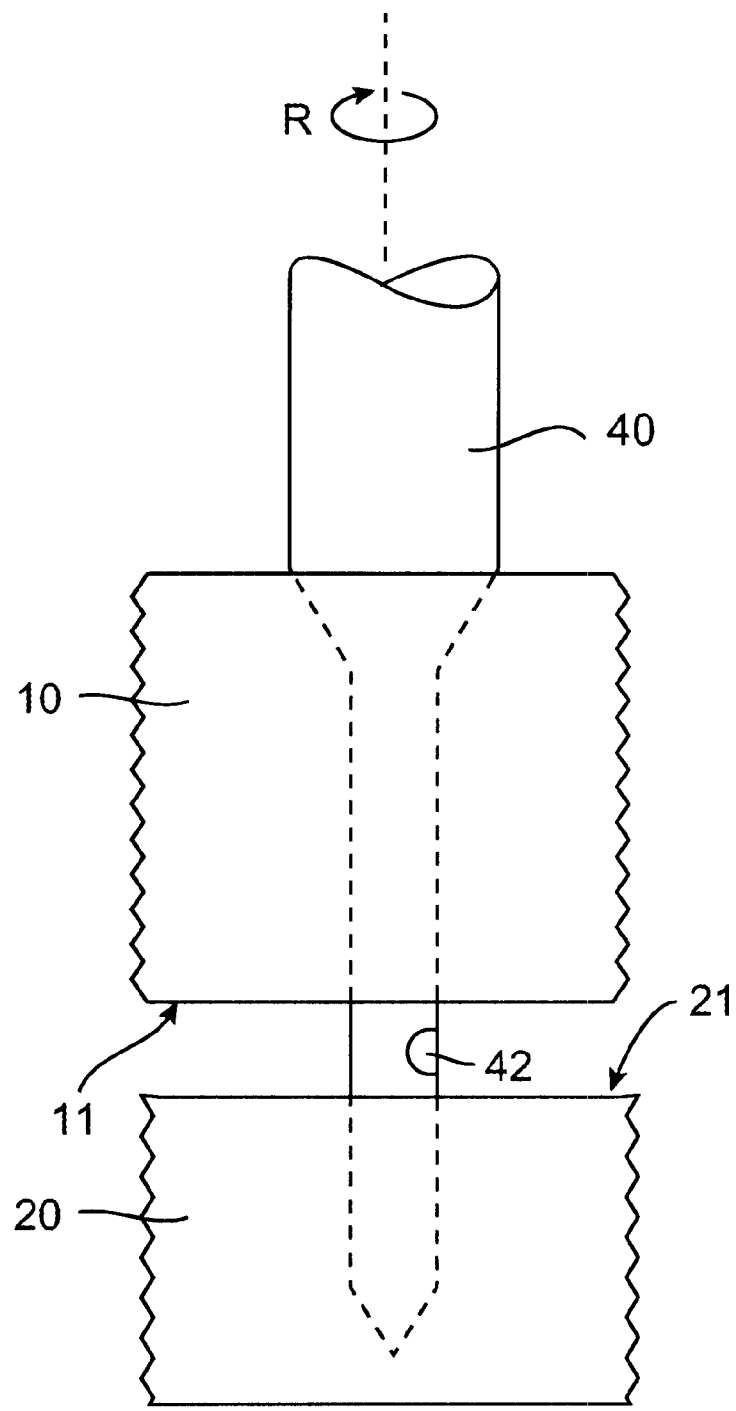
FIG. 4 is an illustration of a drill being advanced through a first facet joint, and into a second facet joint, showing the position of a side hole in the drill with respect to the first and second facet joints.

Drill 40 is rotated in direction R and advanced distally in direction D such that it drills a hole through first facet joint 10 and into second facet joint 20, as illustrated in FIG. 4. Drill 40 has a side opening 42 which is then preferably positioned between adjacent opposite contacting surfaces 11 and 21 of respective facet joints 10 and 20, as shown.

Figure 5:
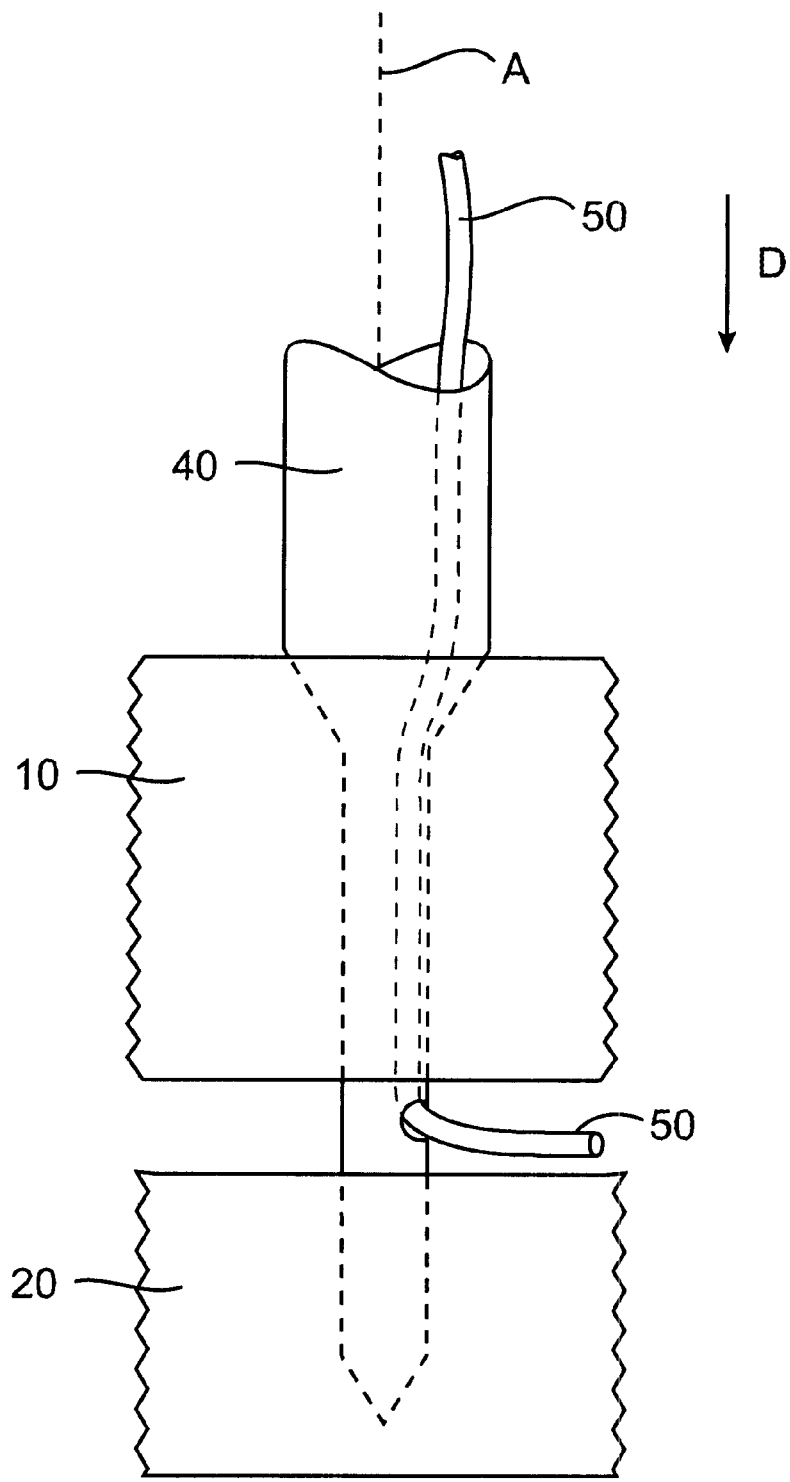
FIG. 5 is an illustration of a an extending member being advanced through a cannulated passageway in the drill such that the distal end of the extending member passes out through the side hole in the drill.

Thereafter, as shown in FIG. 5, an extending member 50, which may preferably comprise a flexible wire, is advanced distally in direction D through a cannulated passageway in drill 40 such that a distal end of extending member 50 protrudes out through side hole 42, and projects radially outward from the central longitudinal axis A of drill 40, as shown.

Figure 6:
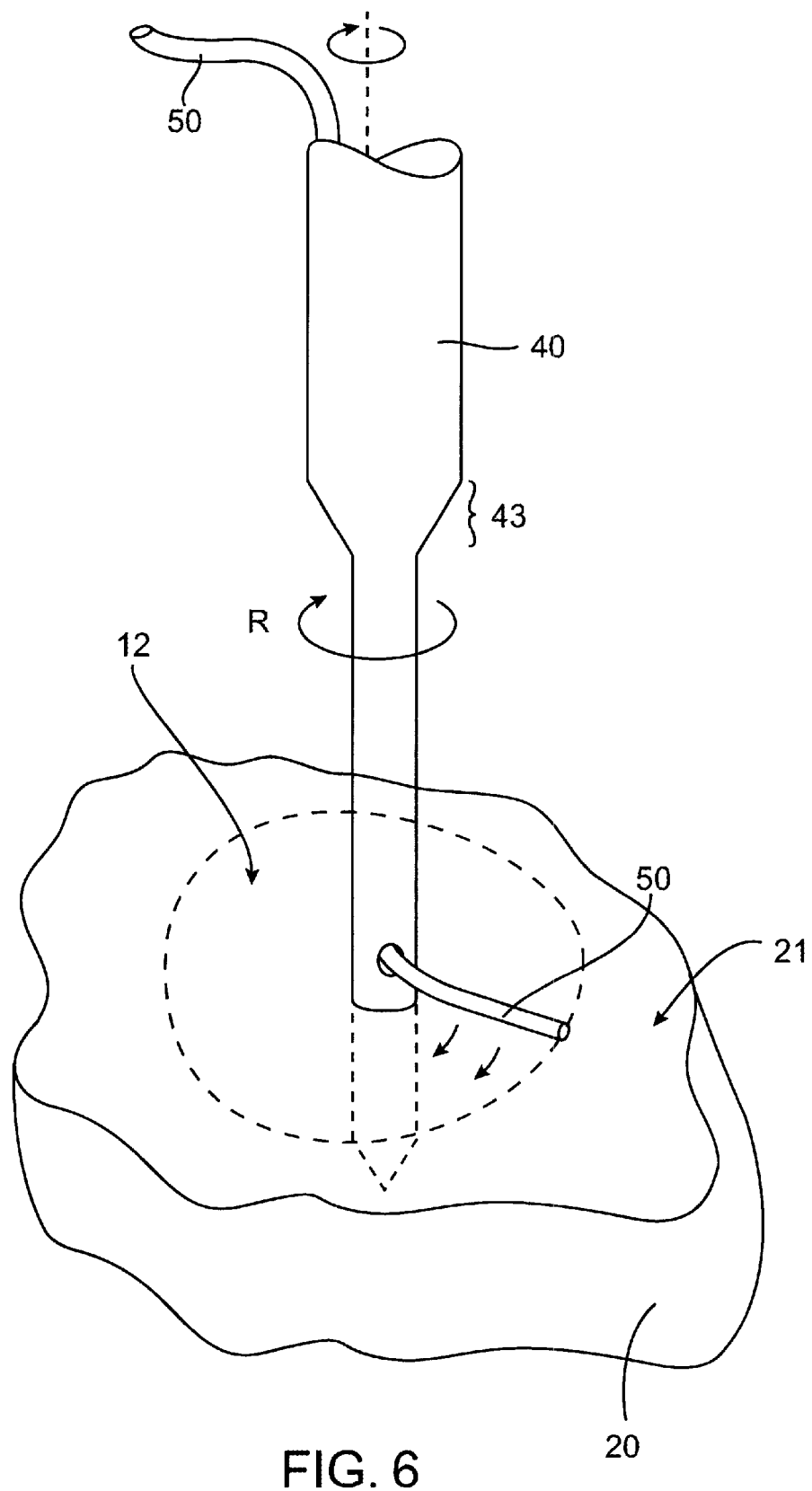
FIG. 6 is an illustration of the rotation of the drill and extending member (with the first facet joint removed for clarity).

As shown in FIG. 6, (with first facet joint 10 removed for clarity), drill 40 is then rotated with extending member 50 protruding radially therefrom. As such, extending member 50 will ablate adjacent opposite contacting surfaces 11 and 21 of respective facet joints 10 and 20. For example, the flexible wire extending member 50 will ablate region 12 (shown bound by dotted lines) on top of surface 11. Similarly, extending member 50 will also ablate a corresponding region of surface 21.

Figure 7:
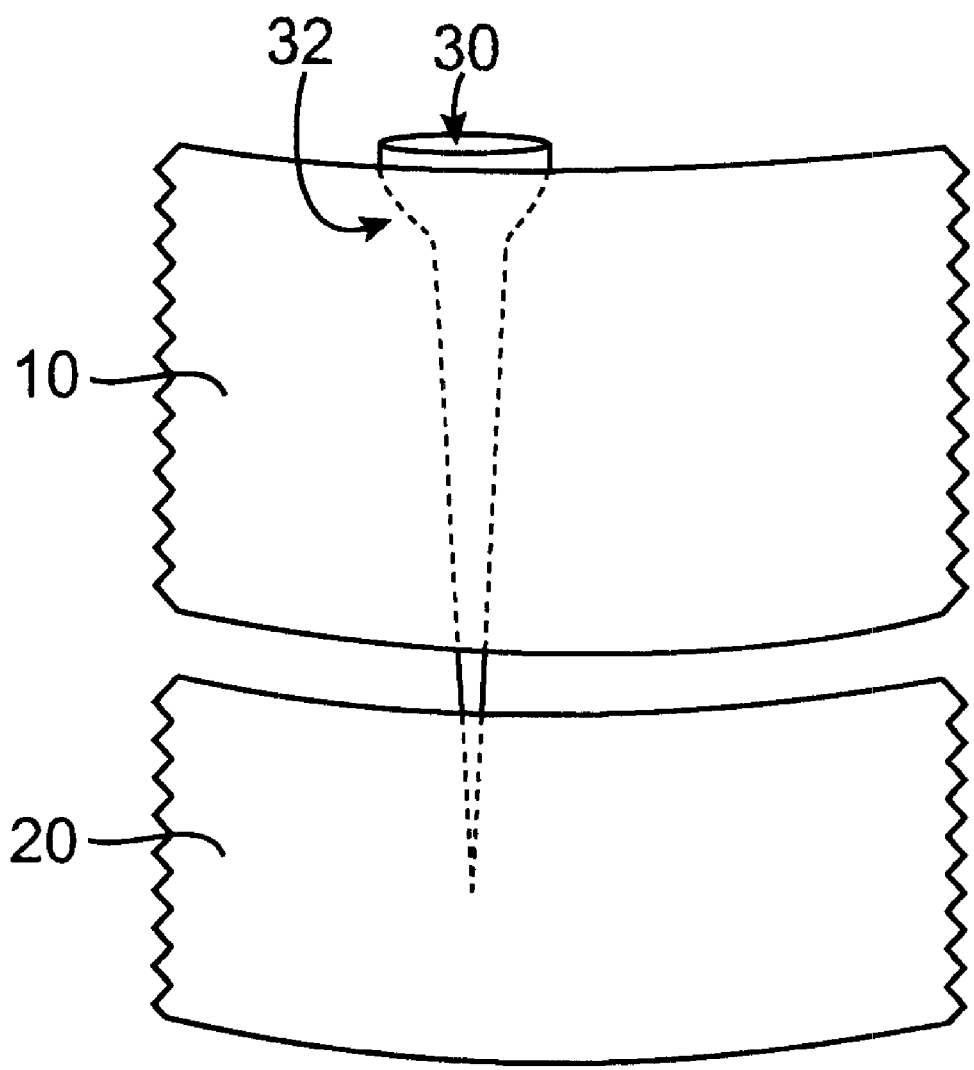
FIG. 7 is an illustration of the placement of the facet screw, passing through the first facet joint and into the second facet joint.

The ablation of such large circular regions of opposite contacting surfaces 11 and 21 will tend to promote a healing response in the bony tissue of the facet joints, such that first facet joint 10 and second facet joint 20 will then tend to fuse together over time. As shown in FIG. 7, drill 40 is then removed and facet screw 30 is then advanced through the hole which had been drilled by drill 40. When tightly screwed into position, relative movement between first facet joint 10 and second facet joint 20 will be effectively inhibited. This, coupled with the fusion between first facet joint 10 and second facet joint 20 promoted by ablation of their contacting surfaces, will provide an effective system for securing a patient's opposing first and second facet joints together.

In an optional preferred aspect of the present invention, drill 40 is dimensioned with a tapered portion 43 along its length such that drill 40 cuts a countersink in first facet joint 10. As shown in FIG. 7, the countersink cut by drill 40 is preferably dimensioned such that head 32 of facet screw 30 can be received therein. Head 32 can thus be positioned to be received generally flat against the surface of first facet joint 10, such that head 32 does not project outwardly into the surrounding tissue.

Figure 8:
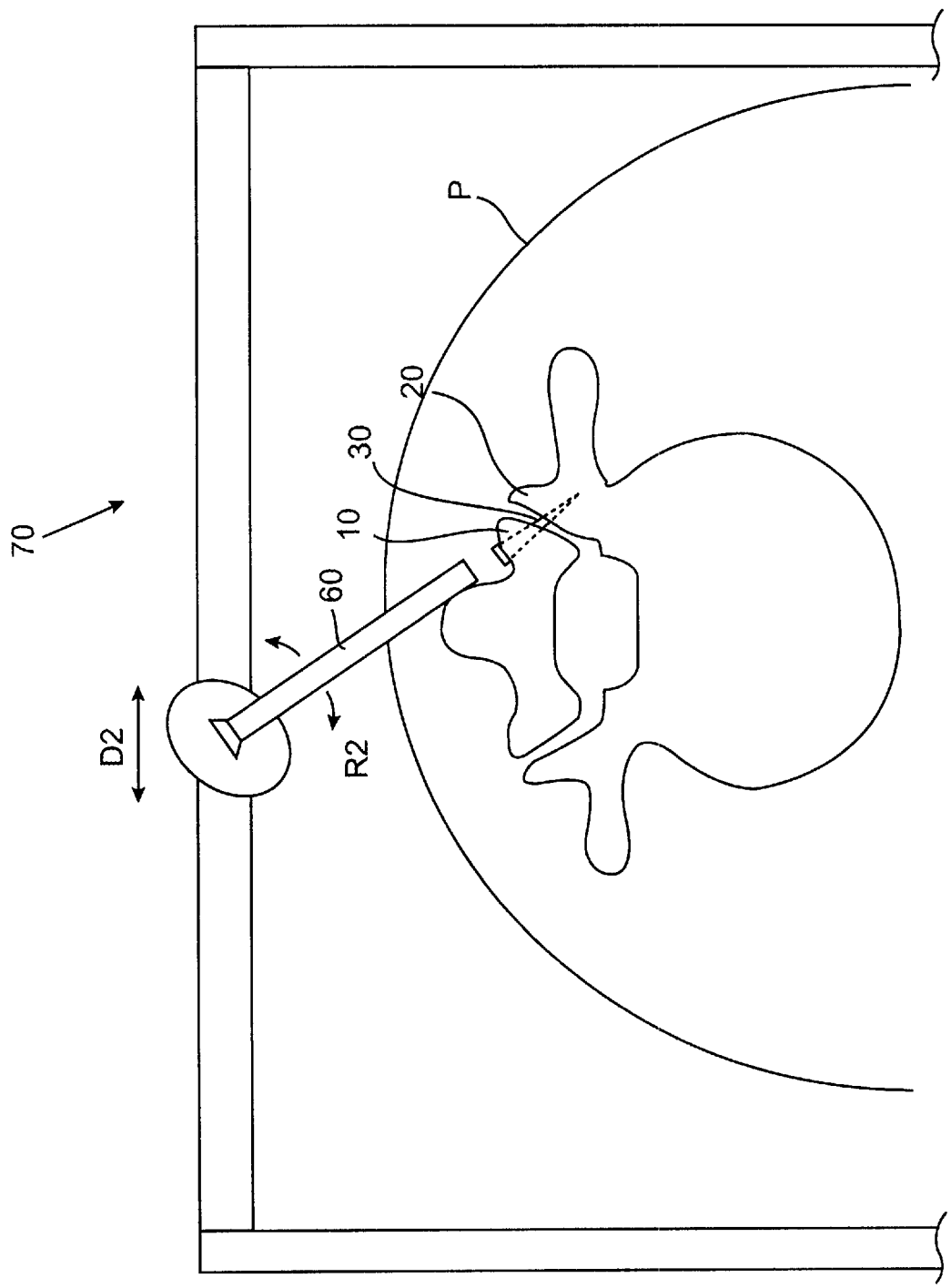
FIG. 8 is an illustration of the placement of the facet screw using a surgical guideframe.

FIG. 8 is an illustration of the placement of facet screw 30 such that it fastens first facet joint 10 and second facet joint 20 together. Facet screw 30 (and drill 40, not shown) are oriented in a preferred posterolateral approach with respect to patient P. Specifically an operating cannula 60 is suspended from a surgical guidance platform 70 such that it can be rotated to desired positions by being rotated in direction R2 and translated to various positions in direction D2. An example of a suitable surgical guidance platform is found in co-pending U.S. patent application Ser. No. 09/326,739 filed Jun. 4, 1999, previously incorporated by reference.

While the exemplary embodiments have been described in some detail, by way of example and for clarity of understanding, a variety changes, adaptations, and modifications will be obvious to those of skill in the art. Hence, the scope of the present invention is limited solely by the appended claims.

What is claimed is:

1. A method of immobilizing a patient's facet joint, comprising:
    drilling a hole through at least one of a first and second articulating surface of said facet joint;
    ablating said first and second articulating surfaces of said facet joint by applying an ablation member between said first and second articulating surfaces, said ablation member extending from a drill; and
    promoting fusion between said first and second articulating surfaces to immobilize said facet joint.

2. The method of claim 1, wherein the step of ablating is performed by:
    extending an extendible ablation member radially outwards from a drill at a location between said first and second articulating surfaces; and
    rotating the drill such that the extendible ablation member moves in a circular path across portions of said articulating surfaces.

3. The method of claim 2, wherein the step of extending an extendible ablation member radially outwards from a drill involves distally advancing an ablation wire received within a cannulated passageway in the drill such that a distal end of the ablation wire extends outwardly through a side hole in said drill.

4. The method of claim 1, wherein, the hole is drilled in a posterolateral approach through the first articulating surface of said facet joint.

5. The method of claim 4, further comprising:
positioning an operating cannula in a posterolateral approach with respect to the patient; and
advancing a drill through the operating cannula such that a distal end of the drill commences drilling at a posterium of said first articulating surface of said facet joint.

6. The method of claim 5, wherein a surgical guideframe is used to position said operating cannula in the posterolateral approach.

7. The method of claim 1, further including the step of drilling a countersink into sand first articulating surface of said facet joint.

8. The method of claim 1 and further, wherein the step of promoting fusion is performed by introducing an elongate element into said hole for the purposes of maintaining said first and second articulating surfaces in contact with one another.

9. The method of claim 8 and further, wherein the step of introducing an elongate member involves introducing a facet screw into said hole.

10. A method of immobilizing a patient's facet joint, comprising:
drilling a hole through at least one of a first and second articulating surface of said facet joint;
ablating said first and second articulating surfaces of said facet joint by (i) extending an extendible ablation member radially outwards from a drill at a location between said first and second articulating surfaces and (ii) rotating the drill such that the extendible ablation member moves in a circular path across portions of said articulating surfaces; and
promoting fusion between said first and second articulating surfaces to immobilize said facet joint.

11. The method of claim 10, wherein the step of extending an extendible ablation member radially outwards from a drill involves distally advancing an ablation wire received within a cannulated passageway in the drill such that a distal end of the ablation wire extends outwardly through a side hole in said drill.

* * * * *